United States Patent [19]

Temple, Jr. et al.

[11] 4,320,131
[45] Mar. 16, 1982

[54] N-[(4-PHENY-1,2,3,6-TETRAHYDROPYRIDIN-1-YL)ALKYLENE]AZASPIROALKANEDIONES AND N-[(4-HYDROXY-4-PHENYLPIPERIDIN-1-YL)ALKYLENE]AZASPIROALKANEDIONES

[75] Inventors: Davis L. Temple, Jr., Evansville; Joseph P. Yevich, Newburgh; Walter G. Lobeck, Jr., Evansville, all of Ind.

[73] Assignee: Mead Johnson & Company, Evansville, Ind.

[21] Appl. No.: 244,426

[22] Filed: Mar. 16, 1981

[51] Int. Cl.³ .................. A61K 31/445; C07D 401/06
[52] U.S. Cl. ....................................... 424/267; 546/16
[58] Field of Search ........................... 546/16; 424/267

[56] References Cited

U.S. PATENT DOCUMENTS

| 3,106,552 | 10/1963 | Grogan et al. | 546/16 |
| 3,398,151 | 9/1968 | Wu | |
| 3,432,499 | 3/1969 | Rice et al. | 546/16 |
| 3,558,777 | 1/1971 | Wu | 424/250 |
| 3,717,634 | 2/1973 | Wu et al. | |
| 3,907,801 | 9/1975 | Wu et al. | 546/16 |
| 3,976,776 | 8/1976 | Wu et al. | 424/251 |
| 4,179,510 | 12/1979 | McCall | 424/267 |
| 4,218,456 | 8/1980 | Wise et al. | 424/263 |
| 4,221,714 | 9/1980 | McKenzie et al. | 260/244.4 |
| 4,250,175 | 2/1981 | McCall | 424/248.51 |

FOREIGN PATENT DOCUMENTS

| 3013 | 12/1964 | France | 546/16 |
| 55/24374 | 11/1980 | Japan . | |

OTHER PUBLICATIONS

Wu et al. "J. Med. Chem." vol. 12, pp. 876–881 (1969).
Wu et al. "J. Med. Chem." vol. 15, pp. 477–479 (1972).

*Primary Examiner*—Robert T. Bond
*Attorney, Agent, or Firm*—Robert H. Uloth; Robert E. Carnahan

[57] ABSTRACT

N-[(4-Phenyl-1,2,3,6-tetrahydropyridin-1-yl)alkylene]azaspiroalkanediones having substituents in the phenyl ring have been synthesized and demonstrate useful tranquilizing properties. N-[(4-Hydroxy-4-phenylpiperidin-1-yl)alkylene]azaspiroalkanediones are intermediates in their synthesis.

9 Claims, No Drawings

N-[(4-PHENY-1,2,3,6-TETRAHYDROPYRIDIN-1-YL)ALKYLENE]AZASPIROALKANEDIONES AND N-[(4-HYDROXY-4-PHENYLPIPERIDIN-1-YL)ALKYLENE]AZASPIROALKANEDIONES

FIELD OF THE INVENTION

N-[(4-Phenyl-1,2,3,6-tetrahydropyridin-1-yl)alkylene]azaspiroalkanediones and N-[(4-hydroxy-4-hydroxy-4-phenylpiperidin-1-yl)alkylene]azaspiroalkanediones are heterocyclic carbon compounds having a sixmembered hetero ring including one nitrogen atom with the spiro system incorporating this hetero ring (Class 546, Subclass 16).

BACKGROUND OF THE INVENTION 8-(4-Phenyl-1-piperazinylalkylene)-8-azaspiro[4,5]-decane-7,9-diones and 3-(4-phenyl-1-piperazinylalkylene)-3-azaspiro[5,5]undecane-2,4-diones have been prepared as psychotropic agents. These are described in:

Wu, Y. H., U.S. Pat. No. 3,398,151 patented Aug. 20, 1968.

Wu, Y. H., U.S. Pat. No. 3,558,777 patented Jan. 26, 1971.

Wu, et al., *J. Med. Chem.*, 12, 876–881 (1969).

The Wu and Wu, et al. compounds incorporate a piperazine ring system in their structures (Formula 3) and in this respect differ from the compounds of this invention (Formula 1 and Formula 2) which contain tetrahydropyridyl and piperidinyl systems, respectively.

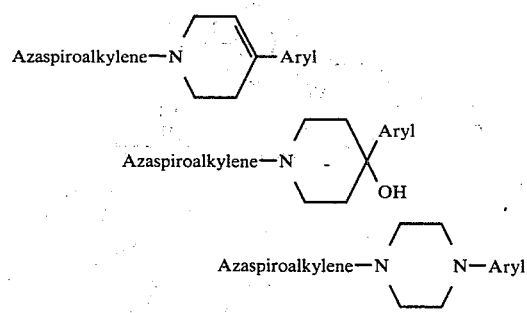

Other variations of the (3) structure, specifically substitution of various heterocycles for the aryl portion, have been described:

Wu, et al., U.S. Pat. No. 3,717,634 patented Feb. 20, 1973.

Wu, et al., U.S. Pat. No. 3,976,776 patented Aug. 24, 1976.

Wu, et al., *J. Med. Chem.*, 15, 447–479 (1972).

Certain 4-substituted-1,2,3,6-tetrahydropyridyl compounds have been described as anti-psychotic agents. Tetrahydropyridylbutyrophenones of formula (4)

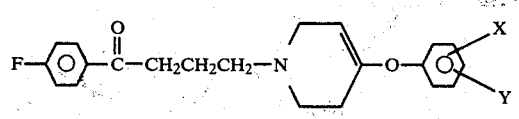

were described in:

Wise, L. D., et al., U.S. Pat. No. 4,218,456 patented Aug. 19, 1980.

These compunds, with butyrophenone- and aryloxy-substituents on the tetrahydropyridine ring, are structurally quite different from compounds comprising the present invention.

Anti-psychotic agents of formula (5) were described in:

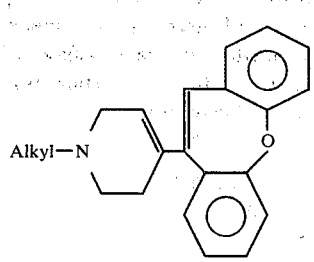

McKenzie, et al., U.S. Pat. No. 4,221,714 patented Sept. 9, 1980.

These compounds, with their particular substituents on the tetrahydropyridine moiety, show increasing dissimilarity of structure compared with the subject compounds of this application.

SUMMARY OF THE INVENTION

This invention is concerned with a new series of CNS-active compounds characterized by the following general structural formula (I) and the non-toxic pharmaceutically acceptable acid addition salts thereof.

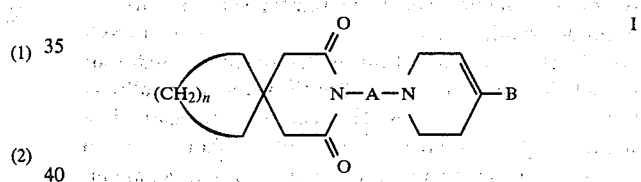

In the foregoing formula, n is the integer 4 or 5; A is a divalent straight alkylene chain of 2 to 5 carbon atoms inclusive; B is

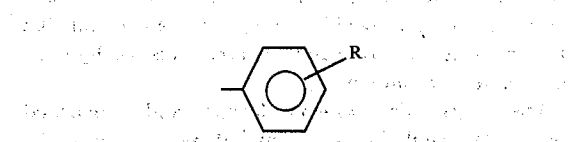

wherein R is hydrogen, lower alkyl from 1 to 4 carbon atoms inclusive, lower alkoxy of from 1 to 4 carbon atoms inclusive, or halogen.

Also disclosed and claimed are compounds of Formula (II) which are useful intermediates for the preparation of (I).

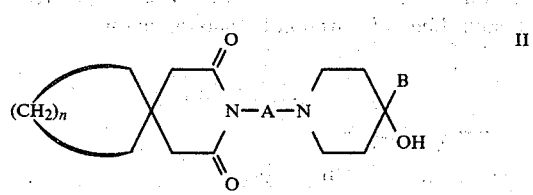

In Formula II, n, A, and B are the same as for formula I.

DETAILED DESCRIPTION OF THE INVENTION

Several processes may be employed for preparation of compounds of Formula I. These processes may be adapted to variation in order to produce other compunds embraced by this invention but not specifically disclosed. Variations of methods to produce the same compounds in somewhat different fashion will also be evident to one skilled in the art. Certain examples will be given for specific illustration.

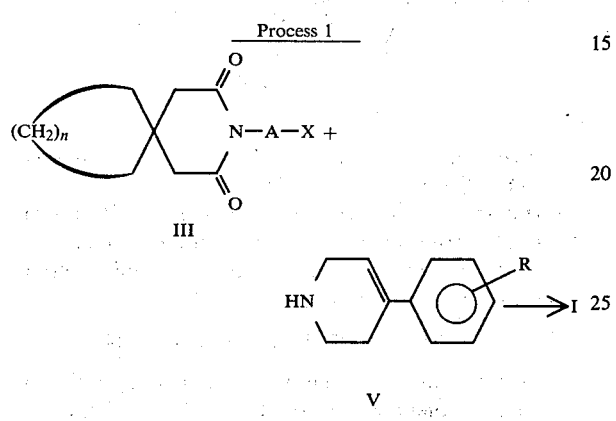

In this scheme, n, A, and R have the same meanings as previously assigned to Formula I. The symbol X refers to a suitable displacement group such as chloride, bromide, iodide, sulfate, phosphate, tosylate, or mesylate. Process 1 is carried out under reaction conditions suitable for the preparation of tertiary amines by alkylation of secondary amines. The reactants are heated in a suitable organic liquid at temperatures of about 60° C. to about 150° C. in the presence of an acid binding agent. Benzene, ethanol, acetonitrile, toluene, and n-butyl alcohol are preferred examples of the organic liquid reaction media. The preferred acid binding agent is potassium carbonate but other inorganic and tertiary organic bases may be employed including other alkali and alkaline earth metal carbonates, bicarbonates, or hydrides and the tertiary amines.

The intermediate azaspirodecane- and undecanediones of Formula III are prepared by reaction of the suitable glutarimide with a dihaloalkane using Process 1 conditions.

The intermediate 4-phenyl-1,2,3,6-tetrahydropyridines of Formula V, some of which are described in the chemical literature or are commercially available, can also be obtained by dehydration, as in the method of Example 3, of 4-phenyl-4-hydroxy-1,2,3,6-tetrahydropyridines of Formula IV shown below.

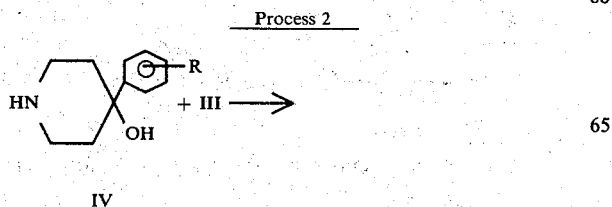

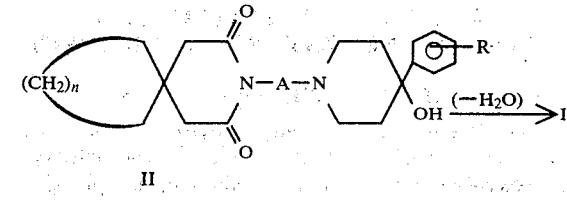

In this scheme, as before, n, A, and R have the same meanings as previously assigned to Formula I. The first step of Process 2, reaction of III and IV, is carried out under conditions similar to Process 1, an identical type of reaction. The second step of Process 2, conversion of II to I, is carried out under reaction conditions appropriate for dehydration reactions. While many processes for dehydration are suitable, such as heating II in $H_3PO_4$ with added $P_2O_5$ (see Example 5), the preferred process involves stirring II in trifluoroacetic acid at ambient room temperature for 12 to 24 hours (see Example 3).

Intermediary 4-phenyl-4-hydroxypiperidines (IV) are prepared according to the following scheme utilizing standard synthetic organic reaction procedures (Grignard agent addition, and catalytic hydrogenolytic debenzylation).

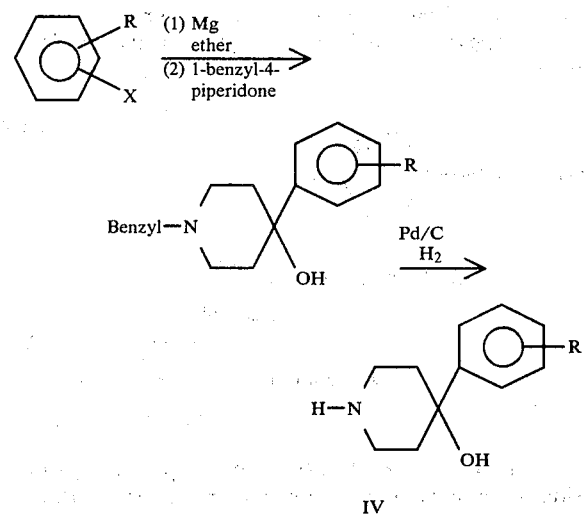

Other processes which may be employed for synthesizing [I] follow.

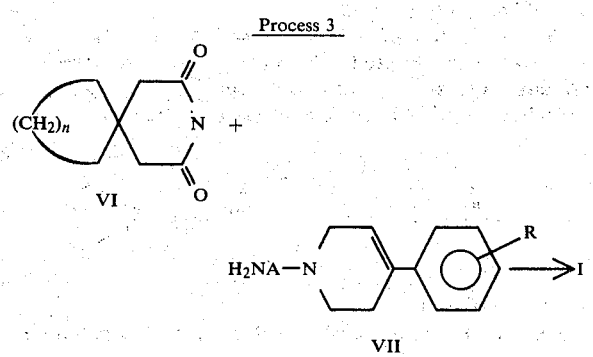

This process, wherein n, A, and R have the same meanings as previously assigned Formula I, consists of reacting a spiro-substituted glutaric anhydride of Formula (VI), many of which are described in chemical literature or are commercially available, with a 1-(ω-aminoalkyl)-4-aryl-1,2,3,6-tetrahydropyridine of Formula (VII). Adaptable methods useful for synthesis of compounds of Formula (V) may be found in the literature or described herein. An example would be reaction of an ω-cyanoalkyl halide with a suitable 4-aryl-1,2,3,6-tetrahydropyridine (or an easily convertable precursor such as IV), followed by reduction of the resulting nitrile to the amine (VII). In general, the reaction of VI and VII is preferably carried out at elevated temperature in an inert organic reaction solvent—pyridine is a preferred solvent. Temperatures in the order of 100° to 200° C. are preferred. A reaction period of at least 2 hrs. may be sufficient, although longer reaction times are customarily employed in the interest of obtaining maximum yield.

Process 4

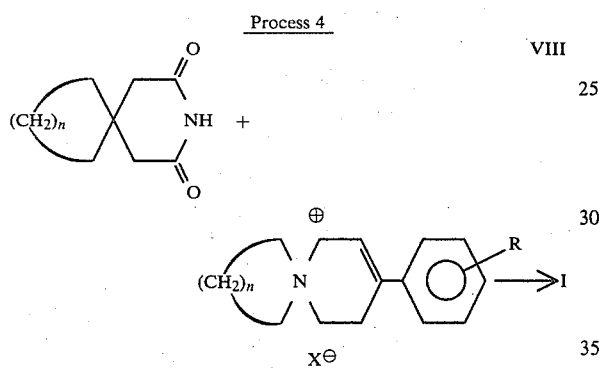

In this embodiment of the subject invention, intermediate compounds of Formula VIII, wherein n, R, and X have the same meanings as given hereinabove, are reacted with a specific glutarimide using conditions described in Process 1, of which this, Process 4, is a variant. Compounds of Formula VIII are prepared by the following scheme.

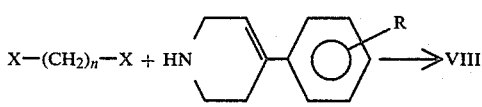

To synthesize compounds of Formula VIII, a 4-aryl-1,2,3,6-tetrahydropyridine (V) is combined with three equivalents of a dihaloalkane in an inert organic solvent in the presence of a strong base. Strong bases which may be employed consist of alkali metal oxides, hydrides, amides, or carbonates with sodium carbonate and potassium carbonate being particularly preferred. Suitable organic solvents, usually with boiling points in the range of about 80° to 160° C., include liquid hydrocarbons, hydrocarbon nitriles, dimethylformamide, hydrocarbon ethers, and the like. The reaction is conveniently carried out at the boiling point of the medium selected. Suitable reaction periods range from 2 to 24 hrs. with the duration of the reaction period depending to some extent upon the temperature and reaction solvent selected. In general, formation of quaternary compounds of Formula VII are facilitated by higher reaction temperatures.

Process 5

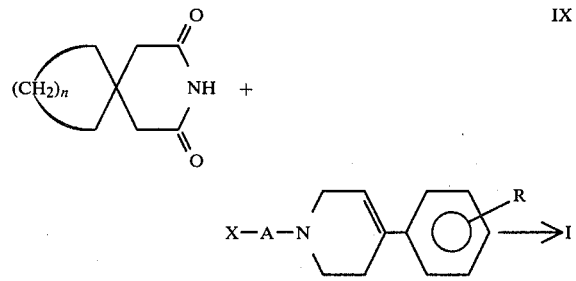

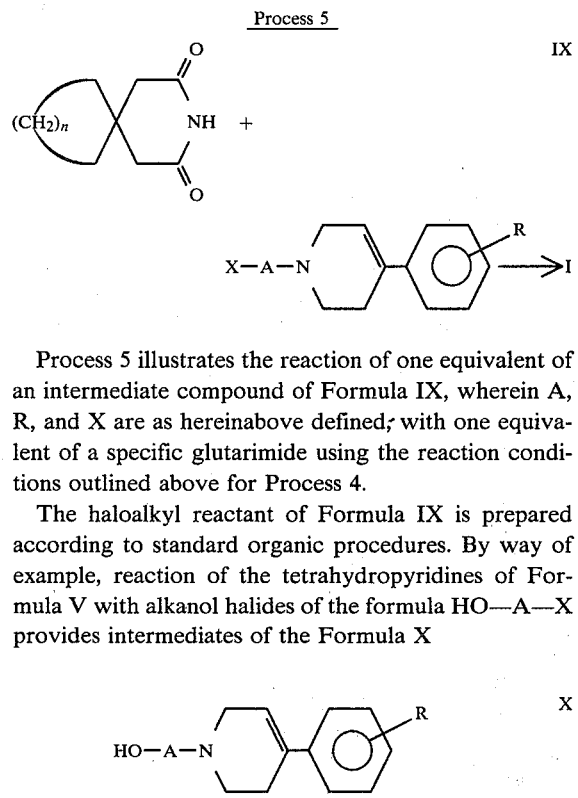

Process 5 illustrates the reaction of one equivalent of an intermediate compound of Formula IX, wherein A, R, and X are as hereinabove defined, with one equivalent of a specific glutarimide using the reaction conditions outlined above for Process 4.

The haloalkyl reactant of Formula IX is prepared according to standard organic procedures. By way of example, reaction of the tetrahydropyridines of Formula V with alkanol halides of the formula HO—A—X provides intermediates of the Formula X This intermediate is then esterified according to conventional techniques well known to the art to provide the Formula IX reactants. For instance, thionyl chloride acting upon the compounds of Formula X provides the Formula IX intermediates in which X is chlorine. In a similar fashion, bromides and iodides are prepared. Phosphates, sulfates, tosylates, mesylates corresponding to Formula IX are obtained with conventional laboratory techniques.

The foregoing embodiments of the process of the present invention for the preparation of compounds of Formula I are considered to be a unitary process. Thus, the 4-phenyltetrahydropyridylalkyleneazaspiroalkanediones of Formula I are prepared in accordance with the unitary process of the present invention by reacting a tetrahydropyridine, or its precursor, depicted by Formula XI

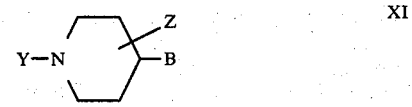

wherein Y is selected from the group consisting of hydrogen (Formula IV and V), H$_2$N—A— (Formula VII), X—A— (Formula IX), or (CH$_2$)$_n$= (Formula VIII), and A, n, and X are as hereinbefore defined; and Z is 4-hydroxy (for the precursor), or Z is a 3,4-double bond; with a spiroglutaric acid derivative, depicted by Formula XII

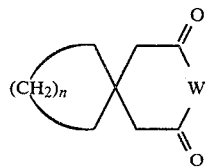

XII wherein n is as hereinbefore defined and W is O (Formula VI) when Y is $H_2N-A-$; or W is N—H when Y is X—A— or $(CH_2)_n=$; or W is N—A—X when Y is hydrogen; in an inert organic liquid medium at an elevated temperature. In the instances when the precursor-type intermediates of Formula XI, Z is 4-hydroxy, were used as reactants, a dehydration step must intervene for preparation of the invention compounds of Formula I.

Biological testing of the subject compounds of formula I in animals demonstrates psychotropic activity of the sort which characterizes tranquilizers. The term tranquilizer used herein encompasses anxioselective and neuroleptic actions. Conventional screening tests can be utilized in determining the psychotropic profile of the instant compounds such as:

1. Conditioned avoidance response in fasted rats treated orally. These data were obtained by the method described in the above Wu, et al. patents and publications.

2. Dopamine receptor binding assay reflecting neuroleptic activity (Burt, Crease, and Synder, Molec. Pharmacol. 12:800 (1976); Burt, Crease, and Snyder, Science 196:326 (1977); Crease, Burt, and Snyder, Science 192:481 (1976).

3. Apomorphine stereotype behavior test in non-fasted rats which determines the ability of centrally acting compounds to block apomorphine-induced stereotyped behavior. This preclinical test gives an indication of potential neuroleptic efficacy (Janssen, et al., Arzneimittel-Forsch., 17:841 (1966)).

The compounds of the present invention may be administered to mammals to exert their anxioselective and neuroleptic effects in the same way and in similar dosage amounts as was suitable for the compounds cited in the above Wu, et al. patents which are incorporated herein in entirety by reference.

Accordingly, another embodiment of the present invention concerns a process for eliciting a tranquilizing effect in a psychotic or neurotic mammal which comprises administering to said mammal a non-toxic effective tranquilizing dose of from 0.01 to 40 mg. per kg. of body weight of said mammal of a Formula I compound or a non-toxic pharmaceutically acceptable acid addition salt thereof.

Appropriate pharmaceutically acceptable carriers, diluents, and adjuvants as set forth in the aforementioned Wu, et al. patents together with the instant compounds may be employed to prepare desired compositions for use in the tranquilizing process. Thus, an embodiment of the invention is directed to a pharmaceutical composition in dosage unit form suitable for systemic administration to a mammalian host comprising a pharmaceutical carrier and an amount of a compound claimed in claim 1 to provide an effective dose of from 0.1 to 40 mg. per kg. of body weight of said host.

DESCRIPTION OF SPECIFIC EMBODIMENTS

The compounds which constitute this invention, their methods of preparation, and their biologic actions will appear more fully from a consideration of the following examples and appended claims which are given for the purpose of illustration only and are not to be construed as limiting the invention in sphere or scope.

In examples which follow, used to illustrate the foregoing processes, temperatures are expressed in degrees centigrade (°). Melting points are uncorrected. The nuclear magnetic resonance (NMR) spectral characteristics refer to chemical shifts ($\delta$) expressed as parts per million (ppm) versus tetramethylsilane (TMS) as reference standard. The relative area reported for the various shifts in the H NMR spectral data corresponds to the number of hydrogen atoms of a particular functional type in the molecule. The nature of the shifts as to multiplicity is reported as broad single (bs), singlet (s), multiplet (m), doublet (d), triplet (t), or doublet of doublets (dd). Abbreviations employed are DMSO-$d_6$ (deuterodimethylsulfoxide), CDCl$_3$ (deuterochloroform), and are otherwise conventional. The infrared (IR) spectral descriptions include only absorption wave numbers (cm$^{-1}$) having functional group identification value. The IR determinations were employed using potassium bromide (KBr) as diluent. The elemental analyses are reported as percent by weight.

EXAMPLE 1

8-[4-(4-Phenyl-1,2,3,6-tetrahydropyridin-1-yl)butyl]-8-azaspiro[4.5]decane-7,9-dione Hydrochloride (Ia; n=4, A=butyl, B=phenyl)

A solution of 0.02 mole each of 4-phenyl-1,2,3,6-tetrahydropyridine (V), 8-(4-bromobutyl)-8-azaspiro[4.5]-decane-7,9-dione (III), and triethylamine in 30 ml. ethanol was heated in a high pressure reaction vessel at 150° C. for 6 hrs., sealed under a nitrogen atmosphere. The reaction solution was evaporated to dryness in vacuo and the residue partitioned between CHCl$_3$ and H$_2$O. The CHCl$_3$ layer was dried (MgSO$_4$), filtered and concentrated to a residue which was dissolved in 20 to 30 ml. ethanol and acidified with ethereal HCl. The solid was collected by filtration and recrystallized from ethanol to give 2.5 g. of the hydrochloride salt, m.p. 215°-217° C.

Anal. Calcd. for C$_{24}$H$_{32}$N$_2$O$_2$.HCl: C, 69.14; H, 7.98; N, 6.72. Found: C, 68.82; H, 7.78; N, 6.60.

NMR (DMSO-$d_6$): 1.52 (12,m); 2.64 (4,s); 3.11 (6,m); 3.68 (4,m); 6.14 (1,m); 7.39 (5,m).

IR (KBr): 690, 745, 1119, 1350, 1360, 1680, 1725, 2570, and 2930 cm$^{-1}$.

EXAMPLE 2

8-(4-Bromobutyl)-8-azaspiro[4.5]decane-7,9-dione (IIIa; n=4, A=butyl, X=Br)

A slurry of 33.4 g. (0.2 mole) of 3,3-tetramethylene glutarimide, 86.4 g. (0.4 mole) of 1,4-dibromobutane, and 89% (0.6 mole) of K$_2$CO$_3$ (pulverized) in 500 ml. toluene was refluxed for 20 hrs. The reaction mixture was filtered while hot. The filtrate was concentrated and distilled in vacuo to afford a 58% yield of product, b.p. 160°-167° C./0.1 mmHg.

EXAMPLE 3

8-[4-(4-[2-Methoxyphenyl]-1,2,3,6-tetrahydropyridin-1-yl)butyl]-8-azaspiro[4.5]decane-7,9-dione Hydrochloride (Ic; n=4, A=butyl, B=2-methoxyphenyl)

8-[4-(4-Hydroxy-4-[2-methoxyphenyl]-1-piperidinyl)-butyl]-8-azaspiro[4.5]dione (IIC, 3 g.) was stirred at room temperature in 20 ml. trifluoroacetic acid for 18 hrs. The reaction solution was concentrated in vacuo to a residue which was partitioned between dilute NH4OH solution and CHCl3. The organic layer was dried (Na2SO4) and concentrated to an oil which was converted to the hydrochloride salt with ethereal HCl in ethanol. The crude salt was isolated and recrystallized twice in acetonitrile-ethyl ether to give 1.5 g. of product (50%), m.p. 159°–161° C.

Anal. Calcd. for $C_{25}H_{34}N_2O_3 \cdot HCl$: C, 67.18; H, 7.90; N, 6.27. Found: C, 67.11; H, 7.68; N, 6.33.

NMR (DMSO-$d_6$): 1.49 (12,m); 2.60 (4,s); 3.04 (6,m); 3.64 (4,m); 3.74 (3,s); 5.74 (1,m); 7.00 (4,m); 11.15 (1,bs).

IR (KBr): 760, 1125, 1255, 1355, 1435, 1670, 1722, 2480, and 2955 cm$^{-1}$.

EXAMPLE 4

8-[4-(4-Hydroxy-4-[2-methoxyphenyl]-1-piperidinyl)-butyl]-8-azaspiro[4.5]decane-7,9-dione Hydrochloride (IIc; n=4, A=butyl, B=2-methoxyphenyl)

4-Hydroxy-4-(2-methoxyphenyl)piperidine (2 g., IVc where R=2-MeO-prepared as set forth below); 8-[4-(1-bromobutyl)]-8-azaspiro[4.5]decane-7,9-dione (2.4 g, IIIa); $K_2CO_3$ (2.3 g.); and KI (0.15 g) were combined in 80 ml. acetonitrile and refluxed for 18 hrs. The reaction mixture was filtered while hot and the filtrate concentrated in vacuo to a residue which was dissolved in 70 ml. CHCl3. The CHCl3 solution was washed twice, using 50 ml. H2O; dried with MgSO4; filtered and concentrated to 3.7 g. of oil. Conversion of the oil to the hydrochloride salt (ethanol and ethereal HCl) and recrystallization from ethanol gave a 73% yield of product, m.p. 246°–248° C.

Anal. Calcd. for $C_{25}H_{36}N_2O_4 \cdot HCl$: C, 64.58; H, 8.03; N, 6.03. Found: C, 64.33; H, 7.82; N, 6.02.

NMR (DMSO-$d_6$): 1.56 (14,m); 2.64 (4,s); 3.10 (8,m); 3.68 (2,m); 3.84 (3,s); 5.30 (1,bs); 7.09 (3,m); 7.54 (1,m); 10.80 (1,bs).

IR (KBr): 755, 1120, 1238, 1350, 1430, 1672, 1720, 2710, 2930, and 3300 cm$^{-1}$.

EXAMPLE 5

8-[4-(4-[4-Chlorophenyl]-1,2,3,6-tetrahydropyridin-1-yl) butyl]-8-azaspiro[4.5]decane-7,9-dione Hydrochloride (Ib; n=4, A=butyl, B=4-chlorophenyl)

8-[4-(4-[4-Chlorophenyl]-4-hydroxy-1-piperidinyl)-butyl]-8-azaspiro[4.5]decane-7,9-dione hydrochloride (II, 2 g) was added in portions to a stirred reaction medium consisting of 2 g. $P_2O_5$ in 10 ml. $H_3PO_4$. After completion of addition the stirred mixture was heated to 170° and kept in that range for 3 hr. After being allowed to cool and stand at room temperature for 12 hours, the reaction mixture was hydrolyzed, while being kept cool with an ice bath, using 10 ml. H2O. The hydrolyzed mixture was made basic, using sat'd $Na_2CO_3$ solution, and extracted with ether. The ether extract was dried (MgSO4) and concentrated to a residual oil which was converted to the hydrochloride salt using a dilute ethanolic solution of HCl. Addition of ether caused precipitation of solid which was collected by filtration and dried to give 0.5 g. product (26%), m.p. 222°–224° C.

Anal. Calcd. for $C_{24}H_{31}ClN_2O_2 \cdot HCl$: C, 63.86; H, 7.15; N, 6.21. Found: C, 63.52; H, 7.18; N, 6.10.

NMR (DMSO-$d_6$): 1.52 (12,m); 2.64 (4,s); 3.12 (6,m); 3.67 (4,m); 6.19 (1,m); 7.45 (4,m); 11.35 (1,bs).

IR (KBr): 810, 1125, 1355, 1670, 1723, 2580, and 2955 cm$^{-1}$.

EXAMPLE 6

8-[4-(4-[4-Chlorophenyl]-4-hydroxy-1-piperidinyl) butyl]-8-azaspiro[4.5]decane-7,9-dione Hydrochloride (IIb; n=4, A=butyl, B=4-chlorophenyl)

4-(4-Chlorophenyl)-4-hydroxypiperidine (4 g., IVb where R=4-Cl-prepared as set forth below); IIIa (5.7 g.,); Et3N (1.9 g.) were all dissolved in 50 ml. ethanol and heated at 150° C. in a sealed reaction vessel for 6 hr. After cooling, the reaction mixture was concentrated to a residue and partitioned between CHCl3 and 1 M NaOH. The CHCl3 layer was separated, dried (MgSO4) and concentrated to 18.6 g. of grease-like residue. This material was dissolved in ethanol and acidified with ethereal HCl. Filtration gave 6.9 g. of HCl salt, m.p. 242°–244° C. (decompose).

Anal. Calcd. for $C_{24}H_{33}ClN_2O_3 \cdot HCl \cdot \frac{1}{4}H_2O$: C, 61.41; H, 7.31; N, 5.97. Found: C, 60.88; H, 7.34; N, 5.88.

What is claimed is:

1. A compound selected from the group consisting of a compound having the formula (I)

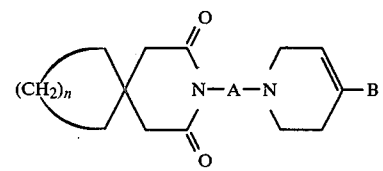

wherein
n is the integer 4 or 5;
A is a divalent straight alkylene chain of 2 to 5 carbon atoms inclusive;
B is

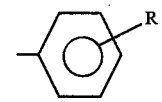

wherein R is hydrogen, lower alkyl from 1 to 4 carbon atoms inclusive, lower alkoxy of from 1 to 4 carbon atoms inclusive, or halogen;

and the non-toxic pharmaceutically acceptable acid addition salts thereof.

2. The compound of claim 1, 8-[4-(4-phenyl-1,2,3,6-tetrahydropyridin-1-yl)butyl]-8-azaspiro[4.5]decane-7,9-dione (Ia) or a pharmaceutically acceptable acid addition salt thereof.

3. The compound of claim 1, 8-[4-(4-[4-chlorophenyl]-1,2,3,6-tetrahydropyridin-1-yl)butyl]-8-azaspiro[4.5]decane-7,9-dione (Ib) or a pharmaceutically acceptable acid addition salt thereof.

4. The compound of claim 1, 8-[4-(4-[2-methoxyphenyl]-1,2,3,6-tetrahydropyridin-1-yl)butyl]-8-azaspiro[4.5]decane-7,9-dione (Ic) or a pharmaceutically acceptable acid addition salt thereof.

5. The process for eliciting a tranquilizer effect in a psychotic or neurotic mammal which comprises administering to said mammal a non-toxic effective tranquilizing dose of from 0.01 to 40 mg. per kg. of body weight of said mammal of a compound claimed in claim 1 by the oral or a parenteral route.

6. A pharmaceutical composition useful for eliciting a tranquilizer effect in dosage unit form suitable for systemic administration to a mammalian host comprising a pharmaceutical carrier and an amount of a compound claimed in claim 1 to provide an effective non-toxic dose of from 0.01 to 40 mg. per kg. of body weight of said host.

7. A compound selected from the group consisting of a compound having the formula (II)

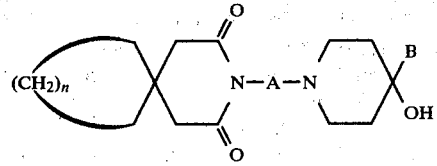

wherein n, A, and B are the same as recited above in claim 1.

8. The compound of claim 7, 8-[4-(4-[4-chlorophenyl]-4-hydroxy-1-piperidinyl)butyl]-8-azaspiro[4.5]-decane-7,9-dione (IIb) or a pharmaceutically acceptable acid addition salt thereof.

9. The compound of claim 7, 8-[4-(4-hydroxy-4-[2-methoxyphenyl]-1-piperidinyl)butyl]-8-azaspiro[4.5]-decane-7,9-dione (IIc) or a pharmaceutically acceptable acid addition salt thereof.

* * * * *